(12) United States Patent
Clouatre (10) Patent No.: US 11,744,814 B2
(45) Date of Patent: Sep. 5, 2023

(54) METHODS AND PHARMACEUTICAL PREPARATIONS FOR ELEVATING BLOOD HEMOGLOBIN AND OXYGEN SATURATION LEVELS WITH HYDROXYCITRIC ACID

(71) Applicant: GLYKON TECHNOLOGIES GROUP, LLC, Seattle, WA (US)

(72) Inventor: Daniel E. Clouatre, Seattle, WA (US)

(73) Assignee: GLYKON TECHNOLOGIES GROUP, LLC, Seattle, WA (US)

( * ) Notice: Subject to any disclaimer, the term of this patent is extended or adjusted under 35 U.S.C. 154(b) by 163 days.

(21) Appl. No.: 17/329,577

(22) Filed: May 25, 2021

(65) Prior Publication Data

US 2021/0369655 A1 Dec. 2, 2021

Related U.S. Application Data

(60) Provisional application No. 63/033,524, filed on Jun. 2, 2020.

(51) Int. Cl.
*A61K 31/194* (2006.01)
*A61B 5/1455* (2006.01)
*G16H 20/10* (2018.01)

(52) U.S. Cl.
CPC ........ *A61K 31/194* (2013.01); *A61B 5/14551* (2013.01); *G16H 20/10* (2018.01)

(58) Field of Classification Search
CPC ... A61K 31/194; G16H 20/10; A61B 5/14551
USPC ....................................................... 514/574
See application file for complete search history.

(56) References Cited

U.S. PATENT DOCUMENTS 5,730,125 A 3/1998 Prutchi et al.
2005/0095233 A1 5/2005 McCleary et al.

FOREIGN PATENT DOCUMENTS

WO WO 2002/078616 10/2002

OTHER PUBLICATIONS

Van Loon et al., "Effects of acute (-)-Hydroxycitrate Supplementation on Substrate Metabolism at Rest and During Exercise in Humans" American Society for Clinical Nutrition (2000) 72:1445-50.

*Primary Examiner* — Kristin A Vajda
(74) *Attorney, Agent, or Firm* — Michael Blessent; Bozicevic, Field & Francis LLP (57) ABSTRACT

Provided is a method of treating a subject, including: (i) determining an initial level of blood oxygen saturation in the subject, and (ii) administering to the subject a therapeutically effective amount of a formulation including HCA, wherein HCA is (−)-hydroxycitric acid, a salt thereof, or a derivative thereof, thereby increasing blood oxygen saturation. Provided is a kit including HCA and instructions directing a subject to ingest the HCA if the subject is determined to have unhealthily low blood oxygen saturation. Provided is a method of treating a subject, including: (i) determining an initial level of blood hemoglobin in the subject, and (ii) administering to the subject a therapeutically effective amount of a formulation including HCA, thereby increasing blood hemoglobin.

19 Claims, 4 Drawing Sheets

METHODS AND PHARMACEUTICAL PREPARATIONS FOR ELEVATING BLOOD HEMOGLOBIN AND OXYGEN SATURATION LEVELS WITH HYDROXYCITRIC ACID

CROSS-REFERENCE TO RELATED APPLICATIONS

This application claims priority to U.S. Provisional Application 63/033,524, filed Jun. 2, 2020, which is incorporated herein by reference.

FIELD OF THE INVENTION

The invention relates generally to the field of medical treatment. More particularly, the invention relates to treating a patient in order to enhance blood oxygen saturation levels and hemoglobin levels by the administration of (−)-hydroxycitric acid, a salt thereof, or a derivative thereof.

BACKGROUND OF THE INVENTION (−)-Hydroxycitric acid, its salts, and its derivatives (collectively: "HCA") are known to have various biological properties. For example, it has been shown that HCA is a competitive inhibitor of ATP citrate lyase, which converts citrate into oxaloacetate and acetyl CoA. One isomer of HCA, (2S,3R)-HCA, inhibits pancreatic alpha-amylase and intestinal alpha-glucosidase, which causes a reduction in carbohydrate metabolism in vitro. HCA has been administered to patients for various medical reasons in the United States in dosages ranging up to approximately 12 grams per day (providing 6-7 grams of HCA).

Separately, many patients suffer from sub-optimal levels of oxygen saturation and blood hemoglobin in their blood. With low oxygen saturation, the fraction of hemoglobin that are saturated with oxygen is relatively low, e.g. less than 90%. For arterial oxygen saturation above 95% there is generally no evidence of any negative health effects. Between 80% and 90% or 95%, however, some impairment of mental function can occur. If the value is 75% or less, loss of consciousness and possibly death can occur.

With low blood hemoglobin, the amount of hemoglobin in blood is relatively low, e.g. less than 130 g/L for a male or less than 120 g/L for a female. Risk factors for developing these conditions include having dementia (e.g., senile dementia, Alzheimer's Disease), insulin resistance, reactive hyperglycemia, diabetes, elevated blood sugar levels, mental stress, or physical stress.

SUMMARY

The inventors have made the surprising discovery that administering HCA causes an increase in oxygen saturation and blood hemoglobin levels in individuals. This action by HCA has not heretofore been recognized even though salts of (−)-hydroxycitric acid have been commercially available for many years and have been administered dosages ranging up to approximately 12 g/day (providing roughly 6-7 g/day of (−)-hydroxycitric acid).

Provided is a method of treating a subject, including: (i) determining an initial level of blood oxygen saturation in the subject, and (ii) administering to the subject a therapeutically effective amount of a formulation including HCA, thereby increasing blood oxygen saturation.

Provided is a kit including HCA and instructions directing a subject to ingest the HCA if the subject is determined to have unhealthily low blood oxygen saturation.

Provided is a method of treating a subject, including: (i) determining an initial level of blood hemoglobin in the subject, and (ii) administering to the subject a therapeutically effective amount of a formulation including HCA, thereby increasing blood hemoglobin.

These and other objects, advantages, and features of the invention will become apparent to those persons skilled in the art upon reading the details of the invention as more fully described below.

Objects and Advantages

It is an objective of the present invention to provide a method for rapidly enhancing blood hemoglobin and blood oxygen saturation levels, for example as shown via fNIRS measurements of the brain, in an individual with suboptimal levels.

These objects and advantages are not derived from the actions commonly claimed for the use of HCA but rather rely upon mechanisms not heretofore uncovered and that yield measurable increases in blood hemoglobin and oxygen saturation levels in as little as 10-15 minutes of ingestion of an appropriate formulation on an empty stomach.

These and other objects, advantages, and features of the invention will become apparent to those persons skilled in the art upon reading the details of the method and formulation as more fully described below.

DETAILED DESCRIPTION

Provided is a method of treating a subject, including: (i) determining an initial level of blood oxygen saturation in the subject, and (ii) administering to the subject a therapeutically effective amount of a formulation including HCA, thereby increasing blood oxygen saturation.

Provided is a kit including HCA and instructions directing a subject to ingest the HCA if the subject is determined to have unhealthily low blood oxygen saturation.

Provided is a method of treating a subject, including: (i) determining an initial level of blood hemoglobin in the subject, and (ii) administering to the subject a therapeutically effective amount of a formulation including HCA, thereby increasing blood hemoglobin.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

HCA includes (−)-hydroxycitric acid, salts thereof, and derivatives thereof. (−)-Hydroxycitric acid itself can be referred as such, or as the free acid of HCA. (−)-Hydroxycitric acid has the CAS number 6205-14-7, the preferred IUPAC name of 1,2-dihydroxypropane-1,2,3-tricarboxylic acid, and the chemical structure shown below. In some cases the salt is recognized as a pharmaceutically acceptable salt.

Blood oxygen saturation is the amount of oxygen-saturated hemoglobin in blood divided by the total amount of hemoglobin in the blood (i.e. saturated plus unsaturated).

Blood oxygen saturation, blood oxygenation level, and oxygen saturation are used interchangeably herein.

The term "subject" and "patient" are used interchangeably herein.

Preferred Embodiments

The free acid form and various salts of (−)-hydroxycitric acid (calcium, magnesium, potassium, sodium, etc. and mixtures thereof) have been available commercially for many years. Any of these materials can be used to fulfill the invention revealed here, but with varying degrees of success. Exact dosing will depend upon the form of HCA used, the weight of the individual involved, metabolism, and the other components of the diet, etc. Due to the advantages of maximizing the uptake and utilization of the HCA salt, enhanced delivery formulations such as U.S. Pat. No. 10,376,483 "Bolus Dose" and U.S. Pat. No. 10,561,630 "Capsule Liquid Delivery" can be used.

Method of Increasing Blood Oxygen Saturation

Provided is a method of treating a subject, including: (i) determining an initial level of blood oxygen saturation in the subject, and (ii) administering to the subject a therapeutically effective amount of a formulation including HCA, thereby increasing blood oxygen saturation.

The amount of HCA necessary to achieve an increase in blood oxygen saturation can vary depending on the individual's body mass, sex, age, health conditions, and other factors. In some cases, the administered HCA is (−)-hydroxycitric acid. In other cases, the administered HCA is a salt or derivative of (−)-hydroxycitric acid.

In some cases, the administered HCA corresponds to 500 mg to 10,000 mg of (−)-hydroxycitric acid, e.g. 1,500 mg to 5,000 mg. For example, if the HCA is (−)-hydroxycitric acid itself, then 500 mg to 10,000 mg of (−)-hydroxycitric acid is administered. However, suppose that the administered HCA is the tri-sodium salt of (−)-hydroxycitric acid. In such a case, since the tri-sodium salt has a molecular weight of 274 g/mol and (−)-hydroxycitric acid is 208 g/mol, then administering 5,000 mg of the tri-sodium salt would correspond to (5,000 divided by 274 multiplied by 208) or 3,796 mg of (−)-hydroxycitric acid.

In some cases, the method further comprises determining an adjusted level of blood oxygen saturation in the subject. Thus, a first determining is performed, and then the administration is performed, and then the second determining of the adjusted level is performed. Any suitable length of time can elapse between each of these steps. For instance, 30 minutes to 300 minutes can elapse between the first determining and the administration. For instance, 10 minutes to 600 minutes can elapse between the administration and the second determining, which is of the adjusted level. The first and subsequent administrations typically, but not necessarily, involve administering the same HCA formulation.

In some cases, the method further comprises performing a second administration of a formulation comprising HCA in an amount based on the difference between the initial level and the adjusted level. For example, if blood oxygen saturation did not measurably change, then a larger amount of HCA can be administered. However, if blood oxygen saturation increased to 100% or nearly 100%, then the second administration can be of a smaller maintenance dose to keep oxygen saturation at or near 100%. This cycle of determining the level of oxygen saturation and administering HCA can be repeated any suitable number of times, with any suitable length of time elapsing between each step. A medical professional can use their professional judgement to determine such factors.

As described above, the HCA can be (−)-hydroxycitric acid, a salt thereof, or a derivative thereof. Suitable salts include sodium, potassium, calcium, magnesium, and potassium-magnesium. Suitable derivates include a lactone, an amide, and an ester. As such, in some cases, the HCA is selected from the group consisting of (−)-hydroxycitric acid, a lactone of (−)-hydroxycitric acid, a sodium salt of (−)-hydroxycitric acid, a potassium salt of (−)-hydroxycitric acid, a calcium salt of (−)-hydroxycitric acid, a magnesium salt of (−)-hydroxycitric acid, a potassium-magnesium salt of (−)-hydroxycitric acid, an amide derivative of (−)-hydroxycitric acid, and an ester derivative of (−)-hydroxycitric acid.

In some case, the HCA is a potassium-magnesium salt of (−)-hydroxycitric acid.

As described above, this method can be used to increase blood oxygen saturation. As such, it is useful for treating subjects with unhealthily low blood oxygen saturation. Due to variations between individuals, what is unhealthy depends upon numerous factors, and as such no single numerical value necessarily separates a healthy blood oxygen saturation level from an unhealthy blood oxygen saturation level. In some cases, prior to the administration, a medical professional determined that the blood oxygen saturation of the patient is unhealthily low. The medical profession can be, for example, a doctor, nurse, or paramedic.

Blood oxygen saturation can be measured in various ways, such as arterial oxygen saturation ($SaO_2$), venous oxygen saturation ($SvO_2$), peripheral oxygen saturation ($SpO_2$), and tissue oxygen saturation ($StO_2$). In some cases, the initial $SaO_2$ is determined to be 90% or less. In some cases, the initial $SvO_2$ is determined to be 60% or less. In some cases a pulse oximeter is used to measure blood oxygen saturation. Although pulse oximeters normally directly measure $SpO_2$, many are configured to give an output that correlates with $SaO_2$. Thus, in some cases, the pulse oximeter measures a $SpO_2$ that correlates with an $SaO_2$ of 90% or less, or the pulse oximeter determines $SaO_2$ to be 90% or less. In other cases, the determining is using infrared spectroscopy, wherein infrared refers to light with a wavelength ranging from 700 nm to 1 mm. For instance, the infrared spectroscopy can be near infrared (NIR) spectroscopy, wherein near infrared light has a wavelength ranging from 700 nm to 1400 nm. In some cases, the infrared spectroscopy is functional spectroscopy, e.g. functional near infrared spectscopy. Exemplary devices for measuring blood oxygen saturation with near infrared spectroscopy are described in U.S. Pat. No. 7,072,701, which is incorporated herein by reference. In some cases, the determining involves obtaining a blood sample from the patient. In some cases, the determining involves performing an arterial-blood gas test (ABG).

In some cases, the subject has been diagnosed by a medical professional with one or more conditions selected from the group consisting of: dementia, insulin resistance, reactive hyperglycemia, diabetes, elevated blood sugar levels, mental stress, and physical stress.

The HCA can be administered in any suitable fashion. For instance, the HCA can be administered orally, e.g. as a solid, as an aqueous solution, in a capsule, or in a pill. Alternatively, the HCA can be administered intravenously or by gastric intubation.

In some cases, the amount of HCA administered is sufficient to increase blood oxygen saturation levels by 5% or more within 1 hour of administration, e.g. by 10% or more, or 25% or more.

In some cases, the administration results in an increase in oxygen saturation such that the subject no longer has unhealthily low oxygen saturation.

In some cases, the method further includes administering triglycerides or coconut oil. In some cases, the method further includes administering a supplement promoting hepatic ketogenesis, e.g. carnitine or alpha-glyceryl phosphoryl choline.

Kit Relating to Blood Oxygen Saturation

Provided is a kit including HCA and instructions directing a subject to ingest the HCA if the subject is determined to have unhealthily low blood oxygen saturation.

If appropriate, each of the aspects discussed above regarding the method of increasing blood oxygen saturation can also be applied to the kit described in this section.

As described above, due to variations between individuals, what is unhealthy depends upon numerous factors, and as such no single numerical value necessarily separates a healthy blood oxygen saturation level from an unhealthy blood oxygen saturation level. However, in some cases, the subject was determined to have an arterial oxygen saturation level ($SaO_2$) of 90% or less. In other cases, a medical professional determined that the subject has an unhealthily low blood oxygen saturation. In some cases, the instructions describe an arterial oxygen saturation level ($SaO_2$) of 89.9% as unhealthily low.

The instructions can be provided in any suitable manner, e.g. as a label attached to a container holding the HCA, or on a piece of paper included in a packaging along with a container holding the HCA. The HCA can be a solid, in an aqueous solution, in a capsule, or in a pill. In some cases, the HCA is in the form of an aqueous solution.

In some cases, the kit further includes a pulse oximeter, and instructions direct the subject to determine the subject's arterial oxygen saturation level ($SaO_2$) with the pulse oximeter.

In some cases, the instructions direct the subject to ingest HCA corresponds to 500 mg to 10,000 mg of (−)-hydroxycitric acid, e.g. 1,500 mg to 5,000 mg. In some cases, the HCA is selected from the group consisting of (−)-hydroxycitric acid, a lactone of (−)-hydroxycitric acid, a sodium salt of (−)-hydroxycitric acid, a potassium salt of (−)-hydroxycitric acid, a calcium salt of (−)-hydroxycitric acid, a magnesium salt of (−)-hydroxycitric acid, a potassium-magnesium salt of (−)-hydroxycitric acid, an amide derivative of (−)-hydroxycitric acid, and an ester derivative of (−)-hydroxycitric acid. In some cases, the HCA is a potassium-magnesium salt of (−)-hydroxycitric acid.

Also provided is method including packaging a formulation including packaging into a container HCA and instructions directing a subject to ingest the HCA if the subject is determined to have unhealthily low blood oxygen saturation. This method corresponds to the kit described in this section, and can include each of the aspects described above relating to the kit.

In some cases, the kit further includes triglycerides or coconut oil. In some cases, the kit further includes administering a supplement promoting hepatic ketogenesis, e.g. carnitine or alpha-glyceryl phosphoryl choline.

Method of Increasing Blood Hemoglobin

Provided is a method of treating a subject, including: (i) determining an initial level of blood hemoglobin in the subject, and (ii) administering to the subject a therapeutically effective amount of a formulation including HCA, thereby increasing blood hemoglobin.

As appropriate, each of the aspects discussed above regarding the method of increasing blood oxygen saturation can also be applied to the methods described in this section, provided that such steps are adapted to blood hemoglobin levels instead of blood oxygen saturation levels.

The amount of HCA necessary to achieve an increase in blood hemoglobin can vary depending on the individual's body mass, sex, age, health conditions, and other factors. In some cases, the administered HCA is (−)-hydroxycitric acid. In other cases, the administered HCA is a salt or derivative of (−)-hydroxycitric acid.

In some cases, the administered HCA corresponds to 500 mg to 10,000 mg of (−)-hydroxycitric acid, e.g. 1,500 mg to 5,000 mg. For example, if the HCA is (−)-hydroxycitric acid itself, then 500 mg to 10,000 mg of (−)-hydroxycitric acid is administered. However, suppose that the administered HCA is the tri-sodium salt of (−)-hydroxycitric acid. In such a case, since the tri-sodium salt has a molecular weight of 274 g/mol and (−)-hydroxycitric acid is 208 g/mol, then administering 5,000 mg of the tri-sodium salt would correspond to (5,000 divided by 274 multiplied by 208) or 3,796 mg of (−)-hydroxycitric acid.

In some cases, the method further comprises determining an adjusted level of blood hemoglobin in the subject. Thus, a first determining is performed, and then the administration is performed, and then the second determining of the adjusted level is performed. Any suitable length of time can elapse between each of these steps. For instance, 30 minutes to 300 minutes can elapse between the first determining and the administration. For instance, 10 minutes to 600 minutes can elapse between the administration and the second determining, which is of the adjusted level.

In some cases, the method further comprises performing a second administration of a formulation comprising HCA in an amount based on the difference between the initial level and the adjusted level. The first and subsequent administrations typically, but not necessarily, involve administering the same HCA formulation. For example, if blood hemoglobin did not measurably change, then a larger amount of HCA can be administered. However, if blood hemoglobin increased by 25% or more, then the second administration can be smaller. This cycle of determining the level of blood hemoglobin and administering HCA can be repeated any suitable number of times, with any suitable length of time elapsing between each step. A medical professional can use their professional judgement to determine such factors.

As described above, the HCA can be (−)-hydroxycitric acid, a salt thereof, or a derivative thereof. Suitable salts include sodium, potassium, calcium, magnesium, and potassium-magnesium. Suitable derivates include a lactone, an amide, and an ester. As such, in some cases, the HCA is selected from the group consisting of (−)-hydroxycitric acid, a lactone of (−)-hydroxycitric acid, a sodium salt of (−)-hydroxycitric acid, a potassium salt of (−)-hydroxycitric acid, a calcium salt of (−)-hydroxycitric acid, a magnesium salt of (−)-hydroxycitric acid, a potassium-magnesium salt of (−)-hydroxycitric acid, an amide derivative of (−)-hydroxycitric acid, and an ester derivative of (−)-hydroxycitric acid.

In some case, the HCA is a potassium-magnesium salt of (−)-hydroxycitric acid.

As described above, this method can be used to increase blood hemoglobin. As such, it is useful for treating subjects with unhealthily low blood hemoglobin. Due to variations between individuals, what is unhealthy depends upon numerous factors, and as such no single numerical value necessarily separates a healthy blood hemoglobin level from an unhealthy blood hemoglobin level. In some cases, prior to the administration, a medical professional determined that the blood hemoglobin of the patient is unhealthily low. The medical profession can be, for example, a doctor, nurse, or paramedic.

Blood oxygen saturation can be measured in any suitable manner. In some cases, the level of blood hemoglobin is less than 130 g/L for a male or less than 120 g/L for a female. In some cases, the initial level of blood hemoglobin is 100 g/L or less.

In some cases, the subject has been diagnosed by a medical professional with one or more conditions selected from the group consisting of: dementia, insulin resistance, reactive hyperglycemia, diabetes, elevated blood sugar levels, mental stress, and physical stress.

The HCA can be administered in any suitable fashion. For instance, the HCA can be administered orally, e.g. as a solid, as an aqueous solution, in a capsule, or in a pill. Alternatively, the HCA can be administered intravenously.

In some cases, the amount of HCA administered is sufficient to increase blood hemoglobin by 5% or more within 1 hour of administration, e.g. by 10% or more, or 25% or more.

In some cases, the administration results in an increase in blood hemoglobin such that the subject no longer has low blood hemoglobin.

In some cases, the method further includes administering triglycerides or coconut oil. In some cases, the method further includes administering a supplement promoting hepatic ketogenesis, e.g. carnitine or alpha-glyceryl phosphoryl choline.

Triglyceride and Cortisol Levels

Provided is a method of treating a subject, including: (i) determining an initial level of triglycerides or cortisol in the subject, and (ii) administering to the subject a therapeutically effective amount of a formulation including HCA, thereby reducing triglycerides, cortisol, or both.

In some cases, the therapeutically effective amount of the formulation comprising HCA is sufficient to produce a 10% decrease in the level of triglycerides or cortisol within 6 hours.

The amount of HCA necessary to achieve an increase in blood oxygen saturation can vary depending on the individual's body mass, sex, age, health conditions, and other factors. In some cases, the administered HCA is (−)-hydroxycitric acid. In other cases, the administered HCA is a salt or derivative of (−)-hydroxycitric acid.

In some cases, the administered HCA corresponds to 500 mg to 10,000 mg of (−)-hydroxycitric acid, e.g. 1,500 mg to 5,000 mg. For example, if the HCA is (−)-hydroxycitric acid itself, then 500 mg to 10,000 mg of (−)-hydroxycitric acid is administered. However, suppose that the administered HCA is the tri-sodium salt of (−)-hydroxycitric acid. In such a case, since the tri-sodium salt has a molecular weight of 274 g/mol and (−)-hydroxycitric acid is 208 g/mol, then administering 5,000 mg of the tri-sodium salt would correspond to (5,000 divided by 274 multiplied by 208) or 3,796 mg of (−)-hydroxycitric acid.

In some cases, the method further comprises determining an adjusted level of triglycerides or cortisol in the subject. Thus, a first determining is performed, and then the administration is performed, and then the second determining of the adjusted level is performed. Any suitable length of time can elapse between each of these steps. For instance, 30 minutes to 300 minutes can elapse between the first determining and the administration. For instance, 10 minutes to 600 minutes can elapse between the administration and the second determining, which is of the adjusted level. The first and subsequent administrations typically, but not necessarily, involve administering the same HCA formulation.

In some cases, the method further comprises performing a second administration of a formulation comprising HCA in an amount based on the difference between the initial level and the adjusted level. For example, if triglycerides or cortisol did not measurably change, then a larger amount of HCA can be administered. However, if blood oxygen saturation decreased measurably, then the second administration can be of a smaller maintenance dose to keep the triglycerides or cortisol at or near the desired range. This cycle of determining the level of triglycerides or cortisol and administering HCA can be repeated any suitable number of times, with any suitable length of time elapsing between each step. A medical professional can use their professional judgement to determine such factors.

As described above, the HCA can be (−)-hydroxycitric acid, a salt thereof, or a derivative thereof. Suitable salts include sodium, potassium, calcium, magnesium, and potassium-magnesium. Suitable derivates include a lactone, an amide, and an ester. As such, in some cases, the HCA is selected from the group consisting of (−)-hydroxycitric acid, a lactone of (−)-hydroxycitric acid, a sodium salt of (−)-hydroxycitric acid, a potassium salt of (−)-hydroxycitric acid, a calcium salt of (−)-hydroxycitric acid, a magnesium salt of (−)-hydroxycitric acid, a potassium-magnesium salt of (−)-hydroxycitric acid, an amide derivative of (−)-hydroxycitric acid, and an ester derivative of (−)-hydroxycitric acid.

In some case, the HCA is a potassium-magnesium salt of (−)-hydroxycitric acid.

As described above, this method can be used to decrease triglycerides or cortisol. As such, it is useful for treating subjects with unhealthily high triglycerides or cortisol. Due to variations between individuals, what is unhealthy depends upon numerous factors, and as such no single numerical value necessarily separates a healthy triglycerides or cortisol level from an unhealthy blood oxygen saturation level. In some cases, prior to the administration, a medical professional determined that the triglycerides or cortisol of the patient is unhealthily high. The medical profession can be, for example, a doctor, nurse, or paramedic.

In some cases, the determining is of triglycerides. For example, the initial level of triglycerides can be determined by a medical professional to be too high. Sometimes the initial level of triglycerides is 150 mg/dL or more, such as 250 mg/dL or more, 400 mg/dL or more, or 500 mg/dL or more.

In some cases, the determining is of cortisol. In some cases, the initial level of cortisol was determined by a medical professional to be unhealthily high. In some cases, the initial level of cortisol was 25 µg/dL or more.

In some cases, the subject has been diagnosed by a medical professional with one or more conditions selected from the group consisting of: dementia, insulin resistance, reactive hyperglycemia, diabetes, elevated blood sugar levels, mental stress, and physical stress.

The HCA can be administered in any suitable fashion. For instance, the HCA can be administered orally, e.g. as a solid, as an aqueous solution, in a capsule, or in a pill. Alternatively, the HCA can be administered intravenously.

In some cases, the amount of HCA administered is sufficient to reduce triglycerides by 5% or more within 6 hours, such as by 10% or more, 20% or more, 30% or more, or 50% or more. In some cases the reduction occurs within 2 hours, such by 5% or more, such as by 10% or more, 20% or more, 30% or more, or 50% or more.

In some cases, the amount of HCA administered is sufficient to reduce cortisol by 5% or more within 6 hours, such as by 10% or more, 20% or more, 30% or more, or 50% or more. In some cases the reduction occurs within 2 hours, such by 5% or more, such as by 10% or more, 20% or more, 30% or more, or 50% or more.

In some cases, the method further includes administering triglycerides or coconut oil. In some cases, the method further includes administering a supplement promoting hepatic ketogenesis, e.g. carnitine or alpha-glyceryl phosphoryl choline.

Kit Relating to Triglycerides

Provided is a kit including HCA and instructions directing a subject to ingest the HCA if the subject is determined to have an unhealthily high triglyceride level.

If appropriate, each of the aspects discussed above regarding the method of reducing triglycerides can also be applied to the kit described in this section.

In some cases, the instructions direct the subject to ingest HCA corresponding to 500 mg to 10,000 mg of (−)-hydroxycitric acid, such as 1,500 mg to 5,000 mg. In some cases, according to the instructions, the unhealthily high triglyceride level is 150 mg/dL or more, such as 250 mg/dL or more, 400 mg/dL or more, or 500 mg/dL or more. HCA can be selected from the group consisting of (−)-hydroxycitric acid, a lactone of (−)-hydroxycitric acid, a sodium salt of (−)-hydroxycitric acid, a potassium salt of (−)-hydroxycitric acid, a calcium salt of (−)-hydroxycitric acid, a magnesium salt of (−)-hydroxycitric acid, a potassium-magnesium salt of (−)-hydroxycitric acid, an amide derivative of (−)-hydroxycitric acid, and an ester derivative of (−)-hydroxycitric acid. Sometimes the HCA is a potassium-magnesium salt of (−)-hydroxycitric acid.

In some cases, the kit further includes a triglyceride measurement device, wherein the instructions direct the subject to determine the triglyceride level with the triglyceride measurement device. In some cases, the triglyceride measurement device also measures cholesterol levels.

The instructions can be provided in any suitable manner, e.g. as a label attached to a container holding the HCA, or on a piece of paper included in a packaging along with a container holding the HCA. The HCA can be a solid, in an aqueous solution, in a capsule, or in a pill. In some cases, the HCA is in the form of an aqueous solution.

Also provided is method including packaging a formulation including packaging into a container HCA and instructions directing a subject to ingest the HCA if the subject is determined to have unhealthily high triglycerides. This method corresponds to the kit described in this section, and can include each of the aspects described above relating to the kit.

In some cases, the kit further includes triglycerides or coconut oil. In some cases, the kit further includes administering a supplement promoting hepatic ketogenesis, e.g. carnitine or alpha-glyceryl phosphoryl choline.

Method of Treating a Sleep Problem

It has been recognized that cortisol levels in an animal typically follow a diurnal cycle, i.e. they increase and decrease according to an endogenous, entrainable oscillation of about 24 hours. This cycle is also sometimes called a circadian rhythm or a diurnal rhythm.

Since administration of HCA has been shown herein to influence cortisol levels, the inventors also provide a method of treating a subject for a sleep problem. In particular, provided is a method of treating a subject, including administering to the subject a therapeutically effective amount of a formulation including HCA, wherein a medical professional has determined that the subject has a sleep problem, thereby reducing the sleep problem. In some cases, this reduction involves a decrease severity of the problem, the frequency of the problem, or both. In some cases, this reduction involves a complete clearance of the problem.

In some cases, the problem is jet lag. Jet lag is a phenomenon wherein a subject quickly moves from one location on Earth to another location on Earth, e.g. via a jet airplane, and therefore the subject's innate 24 hour cycle of hormones and other internal processes is out of sync with the sun cycle at the destination. Administering HCA can help the subject's internal cortisol cycle to become more quickly synced with the 24 hour cycle at the destination. For example, typical cortisol levels are 5 µg/dL to 25 µg/dL at 9 am, and 2.9 µg/dL to 13 µg/dL at midnight. Thus, cortisol levels are somewhat lower at midnight than at 9 am. Thus, in some cases, the administration of HCA can be in the evening (of the destination's time zone), thereby decreasing cortisol levels in the same manner that cortisol levels are decreased naturally. The administration of HCA can be before, after, or both relative to the transit between time zones.

In some cases, the problem is insomnia. HCA can be administered at any suitable time of day.

If appropriate, each of the aspects discussed above regarding the method of reducing cortisol can also be applied to the kit described in this section.

In some cases, the administered HCA corresponding to 500 mg to 10,000 mg of (−)-hydroxycitric acid, such as 1,500 mg to 5,000 mg. HCA can be selected from the group consisting of (−)-hydroxycitric acid, a lactone of (−)-hydroxycitric acid, a sodium salt of (−)-hydroxycitric acid, a potassium salt of (−)-hydroxycitric acid, a calcium salt of (−)-hydroxycitric acid, a magnesium salt of (−)-hydroxycitric acid, a potassium-magnesium salt of (−)-hydroxycitric acid, an amide derivative of (−)-hydroxycitric acid, and an ester derivative of (−)-hydroxycitric acid. Sometimes the HCA is a potassium-magnesium salt of (−)-hydroxycitric acid.

Kit Relating to Cortisol and Sleep

Provided is a kit including HCA and instructions directing a subject to ingest the HCA if the subject has or is expected to have a sleep problem.

If appropriate, each of the aspects discussed above regarding the method of reducing cortisol can also be applied to the kit described in this section.

In some cases, the sleep problem is jet lag. In other cases, the sleep problem is insomnia.

In some cases, the instructions direct the subject to ingest HCA corresponding to 500 mg to 10,000 mg of (−)-hydroxycitric acid, such as 1,500 mg to 5,000 mg. HCA can be selected from the group consisting of (−)-hydroxycitric acid, a lactone of (−)-hydroxycitric acid, a sodium salt of (−)-hydroxycitric acid, a potassium salt of (−)-hydroxycitric acid, a calcium salt of (−)-hydroxycitric acid, a magnesium salt of (−)-hydroxycitric acid, a potassium-magnesium salt of (−)-hydroxycitric acid, an amide derivative of (−)-hydroxycitric acid, and an ester derivative of (−)-hydroxycitric acid. Sometimes the HCA is a potassium-magnesium salt of (−)-hydroxycitric acid.

The instructions can be provided in any suitable manner, e.g. as a label attached to a container holding the HCA, or on a piece of paper included in a packaging along with a container holding the HCA. The HCA can be a solid, in an aqueous solution, in a capsule, or in a pill. In some cases, the HCA is in the form of an aqueous solution.

Also provided is method including packaging a formulation including packaging into a container HCA and instructions directing a subject to ingest the HCA if the subject has or is expected to have a sleep problem. This method corresponds to the kit described in this section, and can include each of the aspects described above relating to the kit.

In some cases, the kit further includes triglycerides or coconut oil. In some cases, the kit further includes administering a supplement promoting hepatic ketogenesis, e.g. carnitine or alpha-glyceryl phosphoryl choline.

Ketone Utilization

Ketone bodies are water-soluble ketone molecules that are produced by the liver from fatty acids. Ketone bodies can be produced at various points in time, such as fasting, starvation, and prolonged exercise. Ketone bodies can also be metabolized by mitochondria in cells in order to provide energy for the cell. Under typical biological conditions, however, mitochondria metabolize glucose in order to provide energy to the cell. For a given amount of energy production, ketone metabolism of BHB (a major ketone) consumes less oxygen than glucose metabolism.

Ketone metabolism is an important biochemical process in the body. As such, if a particular cell is unable to metabolize ketones properly, which can happen for a variety of reasons, the cell might suffer, including cell death.

Administration of HCA can be used to increase ketone utilization. Provided is a method of treating a subject, including: (i) administering to the subject a therapeutically effective amount of a formulation including HCA, wherein a medical professional has hypothesized or determined that the subject is underutilizing ketones, thereby increasing ketone utilization.

Thus, the method can be useful in treating subjects with unhealthily low ketone utilization. Due to variations between individuals, what is unhealthy depends upon numerous factors, and as such no single numerical value necessarily separates a healthy ketone utilization level from an unhealthy ketone utilization level. In some cases, prior to the administration, a medical professional determined or hypothesized that the ketone utilization of the patient is unhealthily low. The medical profession can be, for example, a doctor, nurse, or paramedic.

Some neurological diseases are hypothesized to be caused or worsened by underutilization of ketones. In some cases, the subject has been diagnosed by a medical professional with one or more conditions selected from the group consisting of: dementia, Alzheimer's disease, insulin resistance, reactive hyperglycemia, diabetes, elevated blood sugar levels, mental stress, and physical stress.

The amount of HCA necessary to achieve an increase in ketone utilization can vary depending on the individual's body mass, sex, age, health conditions, and other factors. In some cases, the administered HCA is (−)-hydroxycitric acid. In other cases, the administered HCA is a salt or derivative of (−)-hydroxycitric acid.

In some cases, the administered HCA corresponds to 500 mg to 10,000 mg of (−)-hydroxycitric acid, e.g. 1,500 mg to 5,000 mg. For example, if the HCA is (−)-hydroxycitric acid itself, then 500 mg to 10,000 mg of (−)-hydroxycitric acid is administered. However, suppose that the administered HCA is the tri-sodium salt of (−)-hydroxycitric acid. In such a case, since the tri-sodium salt has a molecular weight of 274 g/mol and (−)-hydroxycitric acid is 208 g/mol, then administering 5,000 mg of the tri-sodium salt would correspond to (5,000 divided by 274 multiplied by 208) or 3,796 mg of (−)-hydroxycitric acid.

As described above, the HCA can be (−)-hydroxycitric acid, a salt thereof, or a derivative thereof. Suitable salts include sodium, potassium, calcium, magnesium, and potassium-magnesium. Suitable derivates include a lactone, an amide, and an ester. As such, in some cases, the HCA is selected from the group consisting of (−)-hydroxycitric acid, a lactone of (−)-hydroxycitric acid, a sodium salt of (−)-hydroxycitric acid, a potassium salt of (−)-hydroxycitric acid, a calcium salt of (−)-hydroxycitric acid, a magnesium salt of (−)-hydroxycitric acid, a potassium-magnesium salt of (−)-hydroxycitric acid, an amide derivative of (−)-hydroxycitric acid, and an ester derivative of (−)-hydroxycitric acid.

In some case, the HCA is a potassium-magnesium salt of (−)-hydroxycitric acid.

The HCA can be administered in any suitable fashion. For instance, the HCA can be administered orally, e.g. as a solid, as an aqueous solution, in a capsule, or in a pill. Alternatively, the HCA can be administered intravenously.

In some cases, the method further includes administering triglycerides or coconut oil. In some cases, the method further includes administering a supplement promoting hepatic ketogenesis, e.g. carnitine or alpha-glyceryl phosphoryl choline.

Kit Relating to Athletic Performance

Provided is a kit including HCA and instructions directing a subject to ingest the HCA if the subject desires increased athletic performance.

If appropriate, each of the aspects discussed above regarding the method of increasing ketone utilization.

In some cases, the athletic performance is aerobic endurance. In some cases, the athletic performance is quicker recovery after exercise.

In some cases, the instructions direct the subject to ingest HCA corresponding to 500 mg to 10,000 mg of (−)-hydroxycitric acid, such as 1,500 mg to 5,000 mg. HCA can be selected from the group consisting of (−)-hydroxycitric acid, a lactone of (−)-hydroxycitric acid, a sodium salt of (−)-hydroxycitric acid, a potassium salt of (−)-hydroxycitric acid, a calcium salt of (−)-hydroxycitric acid, a magnesium salt of (−)-hydroxycitric acid, a potassium-magnesium salt of (−)-hydroxycitric acid, an amide derivative of (−)-hydroxycitric acid, and an ester derivative of (−)-hydroxycitric acid. Sometimes the HCA is a potassium-magnesium salt of (−)-hydroxycitric acid.

Also provided is method including packaging a formulation including packaging into a container HCA and instructions directing a subject to ingest the HCA if the subject desires increased athletic performance. This method corresponds to the kit described in this section, and can include each of the aspects described above relating to the kit.

In some cases, the kit further includes triglycerides or coconut oil. In some cases, the kit further includes administering a supplement promoting hepatic ketogenesis, e.g. carnitine or alpha-glyceryl phosphoryl choline.

Additional Aspects

Also provided are compositions for use in treating a subject for any of the situations described herein. Also provided are the use of HCA in the manufacture of a medicament for the treatment of any of the situations described herein.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1—Creating an HCA Formulation

An aqueous formulation was created that included purified water, a potassium-magnesium salt of (−)-hydroxycitric acid, glycerol, and limonene according to the procedure of U.S. Pat. No. 10,376,483. First, 1.25 ml of glycerol was combined with 3.75 ml of purified water, yielding 5 ml of liquid. Next, 1,500 mg of a potassium-magnesium salt of (−)-hydroxycitric acid was added to the water-glycerol mixture. Since the HCA salt was approximately 69.7% hydroxycitrate, this corresponds to about 1,047 mg of (−)-hydroxycitric acid. Lastly, 20 mg of limonene was added and the liquid was stirred until all items are dissolved and stable. Limonene is a monoterpene that can be used to modify the viscosity of the liquid, e.g. to adjust for nozzle size and filling speed if the aqueous formulation is put into a capsule.

Example 2—Effect of the Example 1 Formulation on Blood Hemoglobin and Oxygen Saturation Subjects 1-4 were orally administered the formulation of Example 1. The Subjects were given either one or two administrations of 8.33 ml of the aqueous formulation of Example 1 on an empty stomach, i.e. wherein with each 8.33 ml the subject received 2,500 mg of the potassium-magnesium (−)-hydroxycitric acid salt, corresponding to 1745 mg of (−)-hydroxycitric acid.

fNIRS testing (functional Near Infrared Spectroscopy) was used to measure blood hemoglobin and oxygen saturation. fNIRS can be used to determine real-time peripheral and cerebral hemodynamic responses. For example, relative changes in HbR (deoxygen saturation), HbO (oxygen saturation), and HbT (total hemoglobin concentration), etc. can be determined via application of Modified Beer Lambert Law. HbR, Hb=deoxygen saturation (shown as the thinnest and bottom dashed line in FIG. 1) HbO, HbO2=oxygen saturation (shown as the medium-thickness and middle line in FIG. 1) HbT=total hemoglobin concentration (shown as the darkest, thickest and top line in FIG. 1). On the graphs, time is in seconds.

Figure 1:
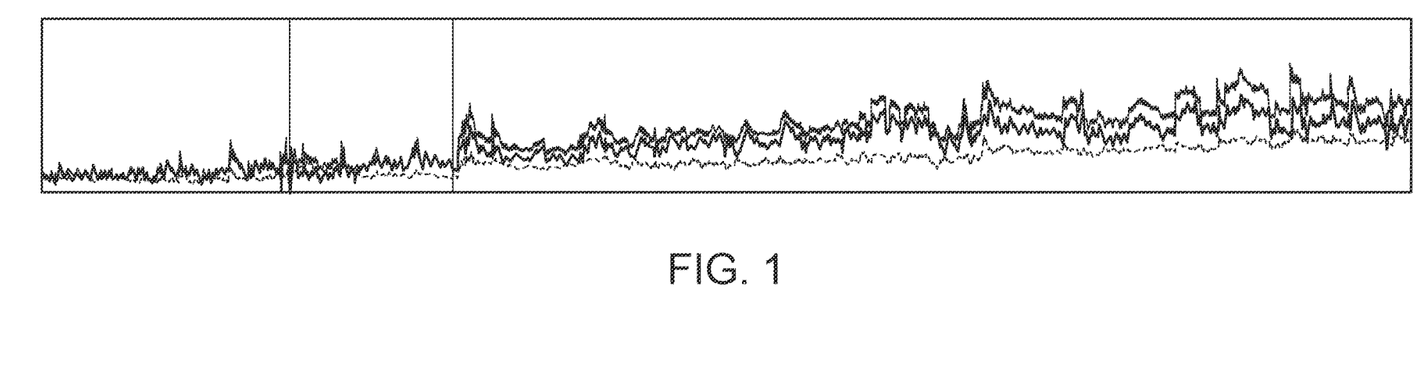
FIG. 1 shows a fNIRS (functional Near Infrared Spectroscopy) measurement of Subject 1, middle-aged male who consumed one "Bolus Dose Shot" containing 2.5 grams of potassium-magnesium HCA salt. Testing was performed via fNIRS. The section before the first vertical line is the reference or baseline period. This line also marks the dosing point. The section after the second vertical line indicates a rather dramatic change in blood hemoglobin and oxygen levels that began 12-15 minutes following dosing. The top, thickest line is HbT=total hemoglobin concentration, the middle line is HbO or HbO2 (oxygen saturation), and the bottom thinnest line is deoxygen saturation.

FIG. 1 shows the results of administration to Subject 1, a middle-aged male. The section before the first vertical line is the reference or baseline period. This line also marks the dosing point. The section after the second vertical line indicates a rather dramatic change in blood hemoglobin and oxygen levels that began 12-15 minutes following dosing.

Figure 2:
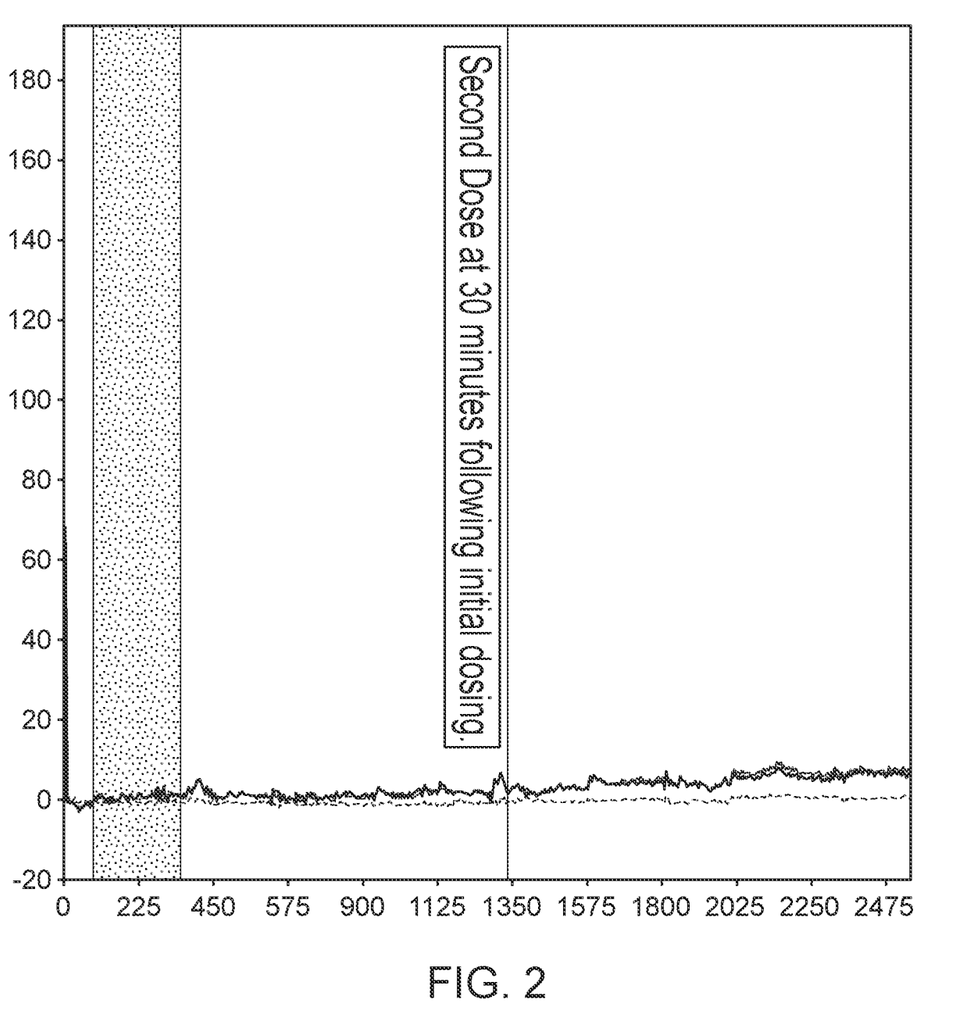
FIG. 2 shows a fNIRS measurement of Subject 2, male in late 50s who first consumed one "Bolus Dose Shot" containing 2.5 grams of potassium-magnesium HCA salt followed by a second "Bolus Dose Shot" thirty minutes after the first. The lines are, from thickest to thinnest, are Hbt, HbO, deoxygen saturation.

FIG. 2 shows the results of administration to Subject 2, a late-50s male. The vertical lines correspond to a first administration of 8.33 ml and a second administration of another 8.33 ml. Blood hemoglobin and oxygen saturation levels increased.

Figure 3:
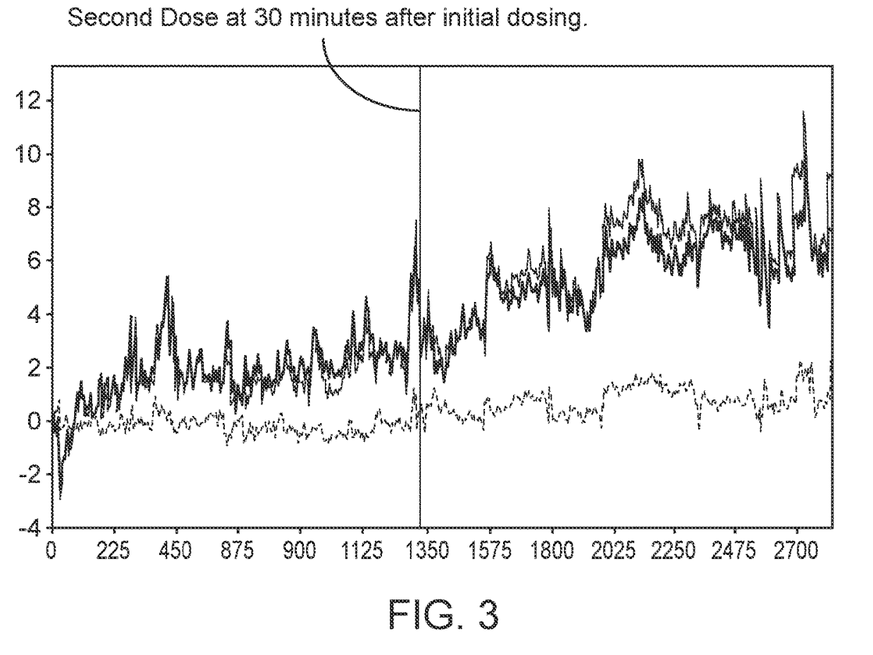
FIG. 3 shows a fNIRS of Subject 3, male, approximately 50 years old, who first consumed one "Bolus Dose Shot" containing 2.5 grams of potassium-magnesium HCA salt followed by a second "Bolus Dose Shot" thirty minutes after the first. The lines are, from thickest to thinnest, are Hbt, HbO, deoxygen saturation.

FIG. 3 shows the results of the administration to Subject 3, a male approximately 50 years old. The first administration of 8.33 ml is at the start of the graph and a second administration of another 8.33 ml is at the vertical line. Blood hemoglobin and oxygen saturation levels increased.

Figure 4:
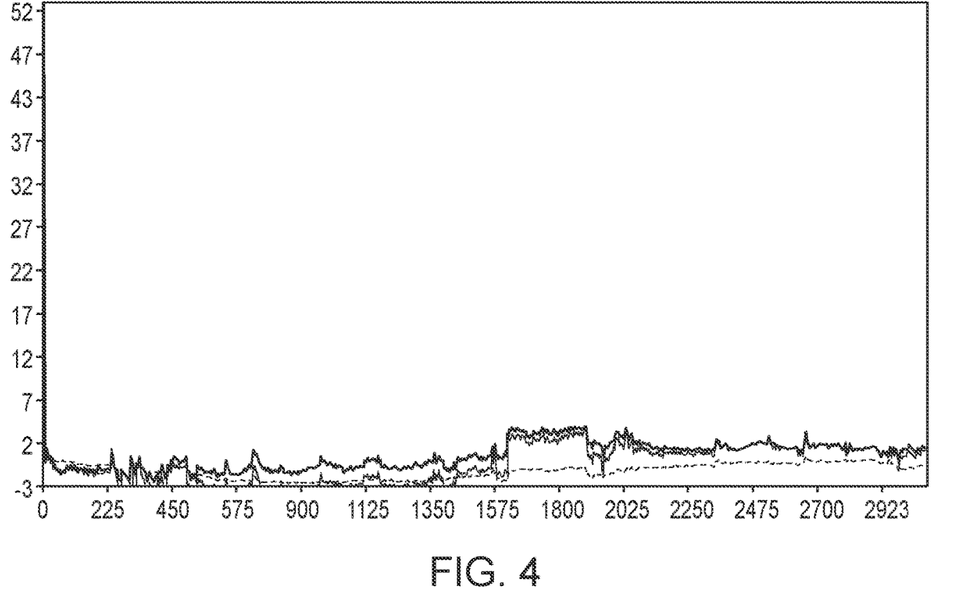
FIG. 4 shows a fNIRS of Subject 4, female of approximately thirty years of age who consumed one "Bolus Dose Shot" containing 2.5 grams of potassium-magnesium HCA salt with testing via fNIRS. The lines are, from thickest to thinnest, are Hbt, HbO, deoxygen saturation.

FIG. 4 shows the results of the administration to Subject 4, a female of approximately 30 years. Blood hemoglobin and oxygen saturation levels increased.

Example 3—Effect of the Example 1 Formulation on Levels of Biomolecules, Such as Triglycerides, Cortisol, and Ketones Subject 5 was a late-60s male, weighing approximately 285 pounds and with a normal fasting blood sugar level of 115-120. First, blood was drawn from Subject 5 and levels of various biomolecules were measured. Next, Subject 5 was administered 16.66 ml of the Example 1 formulation on an empty stomach, i.e. wherein with each 16.66 ml the subject received 5,000 mg of the potassium-magnesium (−)-hydroxycitric acid salt, corresponding to 3490 mg of (−)-hydroxycitric acid. 90 minutes after the administration, blood was drawn from Subject 5 and levels of the various biomolecules were remeasured. The results are shown in the table below.

As can be seen from the table, triglycerides decreased from 1.59 to 0.95, for a net change of minus 0.64 and a percentage change of minus 67%. As also shown in the table, cortisol decreased from 336 to 281, for a net change of minus 55 and a percentage change of minus 20%.

Since triglycerides are metabolized into ketones, it was hypothesized that decreased triglyceride levels would coincide with an increase in ketone levels. In contrast, however, ketone levels decreased from 0.6 to 0.5 after administration of HCA. In essence, the ketone levels stayed the same or experienced a minor decrease after HCA administration. Therefore, it was hypothesized that HCA administration not only produced more ketones from triglycerides, but resulted in an even larger increase the metabolisms of ketones by mitochondria to produce energy. Since mitochondria normally metabolize glucose to generate energy, the glucose was replaced with ketones. Furthermore, the fact that metabolizing some ketones consumes less oxygen provides a possible explanation of why other subjects (in Example 2) experienced increased blood oxygen saturation upon HCA administration.

Figure 5:
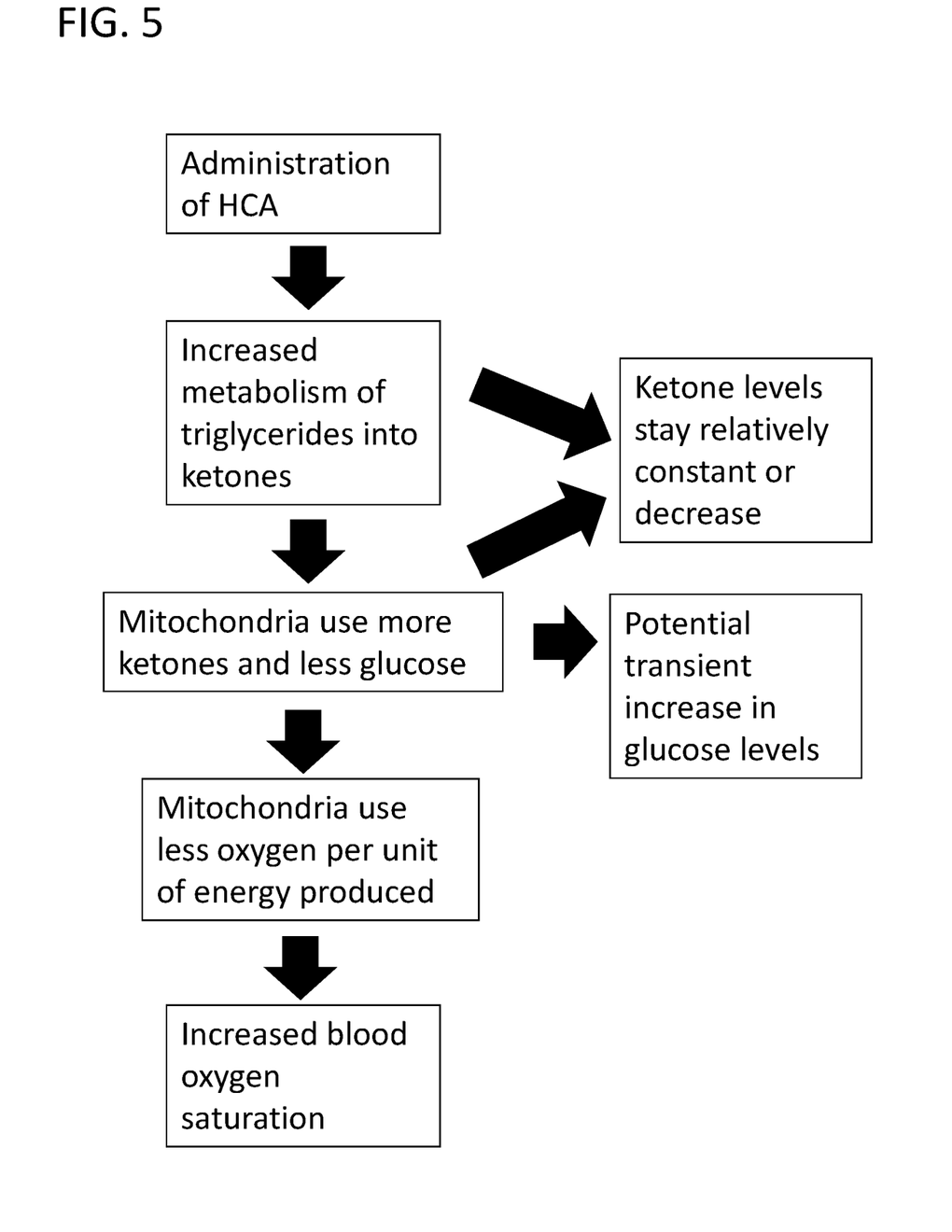
FIG. 5 shows a hypothesized mechanism for the biochemical effects of HCA administration.

As such, the overall hypothesized mechanism is shown in FIG. 5. Namely, administration of HCA increases the metabolism of triglycerides into ketones. In addition, mitochondria use more ketones and less glucose to generate energy. Since metabolizing ketones can sometimes consume less oxygen, blood oxygen saturation increases.

There was also a significant elevation of the subject's blood sugar levels. It is hypothesized that this transient elevation is due to Randall's Cycle. Since the subject was significantly overweight, in metabolizing the triglycerides quickly, it is possible that the HCA was mobilizing too much energy to be disposed of immediately. In support of this explanation, it is noted that this subject had previously used HCA formulations with the result of keeping his otherwise elevated fasting blood glucose levels in the low- to mid-90s with consistent usage.

Subject 6 was administered 16.66 ml of the Example 1 formulation on an empty stomach, i.e. wherein with each

| Subject 5 Biomarker | Before administration (fasting) Result | 90 mins after administration | | | Normal Range | Units |
|---|---|---|---|---|---|---|
| | | Result | Change | Percentage Change | | |
| Cortisol (9am) | 336 | 281 | −55 | −19.57 | 166-507 | nmol/L |
| HDL | 1.72 | 1.78 | 0.06 | 3.37 | 1.1< | mmol/L |
| HDL % of Total Cholesterol | 31.7 | 33.5 | 1.73 | 5.17 | 20< | % |
| HbA1c | 34.4 | 36.3 | 1.99 | 5.48 | 20-42 | mmol/mol |
| LDL | 2.98 | 3.11 | 0.13 | 4.18 | 0-3 | mmol/L |
| Thyroid Stimulating Hormone (TSH) | 1.56 | 1.26 | −0.3 | −23.81 | 0.27-4.2 | mIU/L |
| Total Cholesterol | 5.42 | 5.32 | −0.1 | −1.88 | 0-5 | mmol/L |
| Triglycerides | 1.59 | 0.95 | −0.64 | −67.37 | 0-1.7 | mmol/L |
| Ketones | 0.6 | 0.5 | | | | |

FSB Values:

U.S. value=UK/Canadian value times 18 (mmol/L× 18=mg/dl).

U.K./Canadian value=U.S. value divided by 18 (mg/dl/18=mmol/L).

16.66 ml the subject received 5,000 mg of the potassium-magnesium (−)-hydroxycitric acid salt, corresponding to 3490 mg of (−)-hydroxycitric acid. 90 minutes after the administration, blood was drawn from Subject 6 and levels of the various biomolecules were remeasured. The results are shown in the table below.

| Subject 6 | Before administration (fasting) | 90 mins after administration (fasting) | | | | |
|---|---|---|---|---|---|---|
| Biomarker | Result | Result | Change | Change | Range | Umts |
| Cortisol (9am) | 376 | 319 | −57 | −15.2% | 166-507 | nmol/L |
| HDL | 1.66 | 1.72 | 0.06 | 3.61% | 1.1< | mmol/L |
| HDL % of Total Cholesterol | 33.7 | 33.4 | −0.27 | −0.80% | 20< | % |
| HbA1c | 34.6 | 35.3 | 0.71 | 2.05% | 20-42 | mmol/mol |
| LDL | 2.81 | 3.03 | 0.22 | 7.83% | 0-3 | mmol/L |
| Thyroid Stimulating Hormone (TSH) | 2.31 | 1.98 | −0.33 | −14.3% | 0.27-4.2 | mIU/L |
| Total Cholesterol | 4.93 | 5.15 | 0.22 | 4.46% | 0-5 | mmol/L |
| Triglycerides | 1.01 | 0.89 | −0.12 | −11.9% | 0-1.7 | mmol/L |

As can be seen from the table, triglycerides decreased from 1.01 to 0.89, for a net change of minus 0.12 and a percentage change of minus 11.9%. As also shown in the table, cortisol decreased from 376 to 319, for a net change of minus 57 and a percentage change of minus 15%.

Example 4—Effect of the Example 1 Formulation on Sleep and Stress

Subject 7 was a 60 year-old male of approximately 6 feet tall and average body mass. He was a cancer survivor who had been treated for esophageal cancer with surgery, chemotherapy, and radiation. After overcoming the cancer, Subject 7 tried ingesting the Example 1 formulations to see if it would help with stress and his disturbed sleep. He stated that he got a buzz in the temples within 15-20 minutes. He further reported tingling in his fingers and toes, which he said was surprising since he had nerve damage in his extremities due to the chemotherapy. He stated that there was a quite noticeable change as a result of ingesting the Example 1 formulation. He also found that the Example 1 formulation helped him sleep better and feel better generally.

Example 5—Effect of the Example 1 Formulation on Athletic Performance and Jet Lag Subject 8 was a medium-build male of approximately 50 years of age. Subject 8 was a distance runner. He consumed 15 ml at a time of the Example 1 formulation. He reported a rapid onset of mental clarity. Within 1-2 days of ingesting the Example 1 formulations, he found that his athletic endurance and recovery improved dramatically to the point that he could run a 10,000 meter course in the morning and then do weight training late in the afternoon on the same day—something he could never do before. He also reported that he suffered little to no jet lag after flying coast-to-coast, which is a regular trip for him.

Subject 9 was a large middle-aged male of approximately 50 years of age and an extreme long-distance runner. He consumed 10-15 ml of the Example 1 formulation at a time and reported that within the first week he had much greater athletic endurance and better recovery.

CONCLUSION

HCA administration was found to result in decreased triglycerides, relatively stable or slightly lower levels of ketones, increased glucose, increased oxygen saturation, increased blood hemoglobin, and decreased cortisol. In some cases, the increase in glucose is transient and only for a short period of time. As shown in FIG. 5, it is hypothesized that HCA directly increases metabolism of triglycerides into ketones, but also the metabolism of ketones by mitochondria such that overall ketone levels stay relatively constant or slightly decrease. Since mitochondria use more ketones, they also metabolize less glucose, leading to an increase in glucose levels. Since mitochondrial metabolism of ketones requires less oxygen that glucose metabolism, blood oxygen saturation increase. It is hypothesized that cortisol decreases and blood hemoglobin increases through separate and not yet elucidated mechanisms.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of treating a subject who has an unhealthily low level of blood oxygen saturation, comprising:
    determining that an initial level of blood oxygen saturation in the subject is unhealthily low; and
    administering to the subject a therapeutically effective amount of a formulation comprising HCA,
    wherein the HCA is (−)-hydroxycitric acid or a salt thereof, thereby increasing blood oxygen saturation.

2. The method of claim 1, wherein the administered HCA corresponds to 500 mg to 10,000 mg of (−)-hydroxycitric acid.

3. The method of claim 2, wherein the administered HCA corresponds to 1,500 mg to 5,000 mg of (−)-hydroxycitric acid.

4. The method of claim 1, further comprising determining an adjusted level of blood oxygen saturation in the subject following the administration of the HCA.

5. The method of claim 4, further comprising administering to the subject a formulation comprising HCA in an amount based on the difference between the initial level and the adjusted level.

6. The method of claim 5, further comprising determining a second adjusted level of blood oxygen saturation in the subject following administration based on the difference between the initial level and the adjusted level.

7. The method of claim 1, wherein the HCA is selected from the group consisting of (−)-hydroxycitric acid, a lactone of (−)-hydroxycitric acid, a sodium salt of (−)-hydroxycitric acid, a potassium salt of (−)-hydroxycitric acid, a calcium salt of (−)-hydroxycitric acid, a magnesium salt of (−)-hydroxycitric acid, and a potassium-magnesium salt of (−)-hydroxycitric acid.

8. The method of claim 7, wherein the HCA is a potassium-magnesium salt of (−)-hydroxycitric acid.

9. The method of claim 1, wherein the blood oxygen saturation is arterial oxygen saturation ($SaO_2$).

10. The method of claim 9, wherein the initial level of arterial oxygen saturation is determined to be 90% or less.

11. The method of claim 1, wherein the blood oxygen saturation is venous oxygen saturation ($SvO_2$).

12. The method of claim 11, wherein the initial level of venous oxygen saturation is determined to be 60% or less.

13. The method of claim 1, wherein the blood oxygen saturation is peripheral oxygen saturation ($SpO_2$).

14. The method of claim 13, wherein the determining comprises pulse oximetry.

15. The method of claim 13, wherein the determined $SpO_2$ correlates with a $SaO_2$ of 90% or less.

16. The method of claim 1, wherein the blood oxygen saturation is tissue oxygen saturation ($StO_2$).

17. The method of claim 1, wherein the subject has been diagnosed by a medical professional with one or more conditions selected from the group consisting of: dementia, insulin resistance, reactive hyperglycemia, diabetes, elevated blood sugar levels, mental stress, and physical stress.

18. A kit comprising:
a plurality of doses of a formulation comprising HCA, wherein the HCA is (−)-hydroxycitric acid or a salt thereof; and
instructions directing a subject to ingest the HCA if the subject is determined to have unhealthily low blood oxygen saturation.

19. A method of treating a subject who has an unhealthily low level of blood hemoglobin, comprising:
determining that an initial level of blood hemoglobin in the subject is unhealthily low; and
administering to the subject a therapeutically effective amount of a formulation comprising HCA,
wherein the HCA is (−)-hydroxycitric acid or a salt thereof,
thereby increasing blood hemoglobin.

* * * * *

UNITED STATES PATENT AND TRADEMARK OFFICE
CERTIFICATE OF CORRECTION

PATENT NO. : 11,744,814 B2
APPLICATION NO. : 17/329577
DATED : September 5, 2023
INVENTOR(S) : Daniel E. Clouatre It is certified that error appears in the above-identified patent and that said Letters Patent is hereby corrected as shown below:

In the Specification

At Line 64 of Column 5, please delete "spectscopy." and insert --spectroscopy.--.

At Line 4 of Column 17, please delete "Change" and insert --Percentage Change--.

At Line 4 of Column 17, please delete "Range" and insert --Normal Range--.

At Line 4 of Column 17, please delete "Umts" and insert --Units--.

In the Claims

At Line 1 of Column 19, in Claim 4, please delete "claim 1 ," and insert --claim 1,--.

At Line 12 of Column 19, in Claim 7, please delete "claim 1 ," and insert --claim 1,--.

At Line 20 of Column 19, in Claim 8, please delete "(–)- hydroxycitric" and insert --(–)-hydroxycitric--.

At Line 21 of Column 19, in Claim 9, please delete "claim 1 ," and insert --claim 1,--.

At Line 29 of Column 19, in Claim 13, please delete "claim 1 ," and insert --claim 1,--.

At Line 3 of Column 20, in Claim 15, please delete "claim 13 ," and insert --claim 13,--.

At Line 7 of Column 20, in Claim 17, please delete "claim 1 ," and insert --claim 1,--.

Signed and Sealed this
Thirteenth Day of February, 2024

Katherine Kelly Vidal
*Director of the United States Patent and Trademark Office*